(12) United States Patent
Goto et al.

(10) Patent No.: US 12,226,232 B2
(45) Date of Patent: Feb. 18, 2025

(54) FLEXIBLE DEVICE, METHOD FOR PRODUCING FLEXIBLE DEVICE

(71) Applicant: NIPPON TELEGRAPH AND TELEPHONE CORPORATION, Tokyo (JP)

(72) Inventors: Toichiro Goto, Musashino (JP); Tetsuhiko Teshima, Musashino (JP); Hiroshi Nakashima, Musashino (JP); Shingo Tsukada, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 590 days.

(21) Appl. No.: 17/605,789

(22) PCT Filed: Apr. 8, 2020

(86) PCT No.: PCT/JP2020/015833
§ 371 (c)(1),
(2) Date: Oct. 22, 2021

(87) PCT Pub. No.: WO2020/217996
PCT Pub. Date: Oct. 29, 2020

(65) Prior Publication Data
US 2022/0192601 A1    Jun. 23, 2022

(30) Foreign Application Priority Data
Apr. 25, 2019 (JP) .................................. 2019-084556

(51) Int. Cl.
*A61B 5/293* (2021.01)
*A61B 5/00* (2006.01)
(Continued)

(52) U.S. Cl.
CPC ............. *A61B 5/6868* (2013.01); *A61B 5/266* (2021.01); *A61B 5/293* (2021.01); *H01L 29/786* (2013.01);
(Continued)

(58) Field of Classification Search
CPC .......... A61B 2562/04; A61B 2562/043; A61B 2562/06; A61B 2562/063;
(Continued)

(56) References Cited

U.S. PATENT DOCUMENTS

2017/0176380 A1    6/2017    Borini et al.

FOREIGN PATENT DOCUMENTS

CN    201803985 U  *  4/2011
JP    2017508958 A     3/2017

OTHER PUBLICATIONS

Pullano et al., EGFET-Based Sensors for Bioanalytical Applications: A Review, 2018, Sensors, 18, 4042; doi: 10.3390/s18114042 (Year: 2018).*

(Continued)

*Primary Examiner* — Eun Hwa Kim
(74) *Attorney, Agent, or Firm* — Harness, Dickey & Pierce, P.L.C.

(57) ABSTRACT

A flexible device (1) includes an insulating substrate (2), a source electrode (3), a drain electrode (4), and an extended gate electrode (5) formed on a surface of the insulating substrate (2) at intervals, a channel (6) arranged at an interval between the source electrode (3) and the drain electrode (4), and a gate dielectric (7) formed so as to cover all of the channel (6) and a part of the extended gate electrode (5), in which the insulating substrate (2) is a flexible thin film having light transmissivity, the extended gate electrode (5) is a carbon material thin film having biocompatibility and light transmissivity, the channel (6) is (Continued)

an organic semiconductor thin film, and the gate dielectric (7) is an ionic liquid or an ionic gel.

16 Claims, 10 Drawing Sheets

(51) Int. Cl.
    *A61B 5/266*         (2021.01)
    *H01L 29/786*       (2006.01)
    *H10K 10/82*         (2023.01)
    *H10K 77/10*         (2023.01)
    *H10K 10/46*         (2023.01)

(52) U.S. Cl.
    CPC ............ *H10K 10/82* (2023.02); *H10K 77/111* (2023.02); *A61B 2562/125* (2013.01); *H10K 10/471* (2023.02); *H10K 10/481* (2023.02)

(58) Field of Classification Search
    CPC ........ A61B 2562/066; A61B 2562/164; A61B 2562/166; A61B 5/29; A61B 5/293; A61B 5/6868; H01L 29/772; H01L 29/78
    See application file for complete search history.

(56) References Cited

OTHER PUBLICATIONS

Tsukuru Minamiki et al., Accurate and reproducible detection of proteins in water using an extended-gate type organic transistor biosensor, Applied Physics Letters, vol. 104, No. 24, 2014.

\* cited by examiner

FLEXIBLE DEVICE, METHOD FOR PRODUCING FLEXIBLE DEVICE

CROSS-REFERENCE TO RELATED APPLICATIONS

This application is a 371 U.S. National Phase of International Application No. PCT/JP2020/015833 filed on Apr. 8, 2020, which claims priority to Japanese Application No. 2019-084556 filed on Apr. 25, 2019. The entire disclosures of the above applications are incorporated herein by reference.

TECHNICAL FIELD

The present invention relates to a flexible device and a method for producing a flexible device.

BACKGROUND ART

With the spread of Internet of Everything (IOE), flexible devices are attracting attention. Among flexible devices, wearable electrodes used for healthcare and medical applications and biosensors that measure the concentrations of oxygen and sugar in blood are contributing to the expansion of the wearable system market. In recent years, following on from skin attachment devices for the living body, research and development is being actively carried out on flexible devices that can be directly attached to in vivo tissue such as the brain and heart and used as biodevices for measuring electrical signals of the living body.

As typical methods for measuring electrical signals of the living body, two-terminal measurement for measuring the current between two electrodes in contact with in vivo tissue, and three-terminal measurement using a field-effect transistor (FET) having three electrodes, namely, a source electrode, a drain electrode, and a gate electrode, are known. Three-terminal measurement is generally more advantageous than two-terminal measurement in terms of high accuracy and stabilization.

As a flexible device having a FET structure, a flexible device having an organic FET structure using an organic semiconductor thin film as a channel arranged between a source electrode and a drain electrode is known. Further, a flexible device having an extended gate type FET structure using an extended gate electrode in which the tip of the gate electrode is extended to a position away from the source electrode and the drain electrode is known. For example, Non Patent Literature 1 discloses a flexible device having an extended gate type organic FET structure using an organic semiconductor thin film as a channel and an extended gate electrode as a gate electrode. In the flexible device disclosed in Non Patent Literature 1, a gold thin film is used as an extended gate electrode.

CITATION LIST

Non Patent Literature

Non Patent Literature 1: Tsukuru Minamiki et al., *APPLIED PHYSICS LETTERS* 104, 243703 (2014)

SUMMARY OF THE INVENTION

Technical Problem

In order to study the behavior of living tissue from various viewpoints, it is preferable to be able to optically observe living tissue, perform photogenetic manipulation, membrane potential imaging, etc. while measuring electrical signals of the living body. However, in flexible biodevices in the related art, since the electrodes are opaque, it is not possible to perform optical observation or light irradiation on living tissue.

The present invention has been made in view of the above circumstances, and an object of the present invention is to provide a flexible device and a method for producing a flexible device, the flexible device being capable of simultaneously performing electrical measurement of living tissue and optical observation or light irradiation of the living tissue.

Means for Solving the Problem

A flexible device according to one aspect of the present invention includes an insulating substrate; a source electrode, a drain electrode, and an extended gate electrode formed on the surface of the insulating substrate at intervals; a channel arranged at an interval between the source electrode and the drain electrode; and a gate dielectric formed so as to cover all of the channel and a part of the extended gate electrode, in which the insulating substrate is a flexible thin film having light transmissivity, the extended gate electrode is a carbon material thin film having biocompatibility and light transmissivity, the channel is an organic semiconductor thin film, and the gate dielectric is an ionic liquid or an ionic gel.

In the electrode according to the aspect of the present invention, the insulating substrate may have a structure in which the light transmittance in the wavelength range of from 300 nm to 4 μm is 70% or more.

Further, in the electrode according to the aspect of the present invention, the extended gate electrode may be a carbon material thin film containing carbon atoms with $sp^2$ hybrid orbitals.

Further, in the electrode according to the aspect of the present invention, the extended gate electrode may be a graphene film.

Furthermore, in the electrode according to the aspect of the present invention, the extended gate electrode may be configured such that the light transmittance in the wavelength range of from 300 nm to 4 μm is 70% or more.

Furthermore, in an electrode according to the aspect of the present invention, the extended gate electrode may be configured such that an adhesion ratio of nerve cells measured by the following method is 50% or more.

Method for Measuring Adhesion Ratio of Nerve Cells 1 mL of a nerve cell suspension is dropped onto the extended gate electrode and allowed to stand for 24 hours in a constant temperature bath adjusted to a temperature of 37° C. and a relative humidity of 100%. After standing, the nerve cell suspension on the glass substrate is removed and phosphate buffered saline is added. Next, cells on the glass substrate are stained with trypan blue, the numbers of live cells and dead cells of the nerve cells are counted, and a proportion of the number of live cells to the total number of cells is calculated as an adhesion ratio of the nerve cells.

A method for producing a flexible device according to another aspect of the present invention includes preparing a laminate having a flexible thin film having light transmissivity and a carbon material thin film having biocompatibility and light transmissivity laminated on the surface of the flexible thin film; forming a source electrode, a drain electrode, and an extended gate electrode by removing a part of the carbon material thin film of the laminate; forming an organic semiconductor thin film at an interval between the source electrode and the drain electrode; and applying an ionic liquid or an ionic gel so as to cover all of the organic semiconductor thin film and a part of the extended gate electrode.

Effects of the Invention

According to the present invention, it is possible to provide a flexible device and a method for producing a flexible device capable of simultaneously performing electrical measurement of living tissue and optical observation or light irradiation of the living tissue.

BRIEF DESCRIPTION OF DRAWINGS

FIG. 3 illustrates electrode forming in the method for producing a flexible device according to an embodiment of the present invention, in which FIG. 3(a) is a plan view and FIG. 3(b) is a cross-sectional view taken along the line III(b) to III(b).

FIG. 4 illustrates electrode forming in a method for producing a flexible device according to an embodiment of the present invention, in which FIG. 4(a) is a plan view, and FIG. 4(b) is a cross-sectional view taken along the line IV(b)-IV(b).

FIG. 5 illustrates electrode forming in a method for producing a flexible device according to an embodiment of the present invention, in which FIG. 5(a) is a plan view, and FIG. 5(b) is a cross-sectional view taken along the line V(b)-V(b).

FIG. 6 illustrates channel forming in a method for producing a flexible device according to an embodiment of the present invention, in which FIG. 6(a) is a plan view, and FIG. 6(b) is a cross-sectional view taken along the line VI(b)-VI(b).

FIG. 7 illustrates channel forming in a method for producing a flexible device according to an embodiment of the present invention, in which FIG. 7(a) is a plan view, and FIG. 7(b) is a cross-sectional view taken along the line VII(b)-VII(b).

FIG. 8 illustrates gate dielectric forming in a method for producing a flexible device according to an embodiment of the present invention, in which FIG. 8(a) is a plan view, and FIG. 8(b) is a cross-sectional view taken along the line VIII(b)-VIII(b).

FIG. 9 illustrates gate dielectric coating layer forming in a method for producing a flexible device according to an embodiment of the present invention, in which FIG. 9(a) is a plan view, and FIG. 9(b) is a cross-sectional view taken along the line IX(b)-IX(b).

DESCRIPTION OF EMBODIMENTS

Hereinafter, embodiments of the present invention will be described in detail with reference to the drawings.
Flexible Device Hereinafter, a flexible device according to an embodiment of the present invention will be described.

Figure 1:
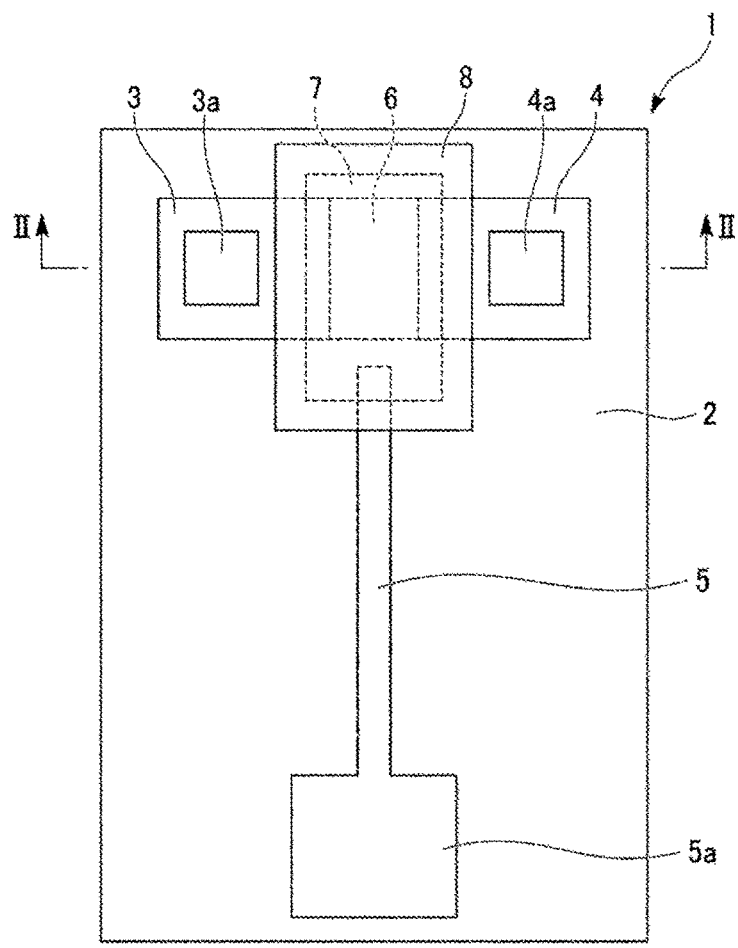
FIG. 1 is a plan view of a flexible device according to an embodiment of the present invention.
Figure 2:
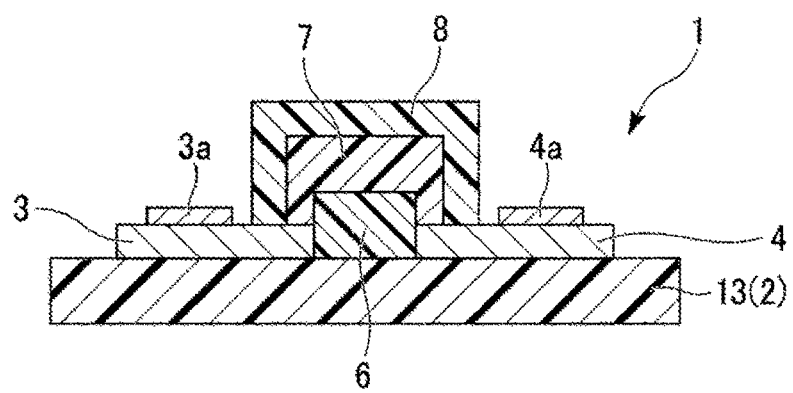
FIG. 2 is a cross-sectional view taken along the line II-II in FIG. 1.

FIG. 1 is a plan view of a flexible device according to an embodiment of the present invention, and FIG. 2 is a sectional view taken along the line II-II of FIG. 1.

As illustrated in FIGS. 1 and 2, a flexible device 1 includes an insulating substrate 2, a source electrode 3, a drain electrode 4, and an extended gate electrode 5 formed on a surface of the insulating substrate 2 at intervals, a channel 6 arranged at an interval between the source electrode 3 and the drain electrode 4, and a gate dielectric 7 formed so as to cover all of the channel 6 and a portion of the extended gate electrode 5. The gate dielectric 7 is covered by a protective layer 8. The source electrode 3 has a source electrode terminal 3a, and the drain electrode 4 has a drain electrode terminal 4a.

The insulating substrate 2 is formed of a flexible thin film 13 having light transmittivity. Although it depends on the application, the insulating substrate 2 preferably has enough flexibility to process the flexible device 1 into an arbitrary shape such as a cylinder or a cone on the whole. The insulating substrate 2 preferably has a light transmittance of 70% or more in a wavelength range of from 300 nm to 4 μm. The insulating substrate 2 is preferably biocompatible and chemically stable.

The material of the insulating substrate 2 is preferably a polyparaxylene resin. The polyparaxylene resin is suitable as a material for the insulating substrate 2 because it has strong resistance to moisture and corrosive gas, can be easily thinned by vapor deposition, and is harmless to in vivo tissue.

The thickness of the insulating substrate 2 is typically from 1 μm to 3 μm.

The source electrode 3 and the drain electrode 4 are formed of a conductive thin film. The source electrode 3 and the drain electrode 4 may be formed of a carbon material thin film described later, similarly to the extended gate electrode 5. Further, the source electrode 3 and the drain electrode 4 may be formed of a metal thin film, a conductive oxide thin film, and a conductive polymer thin film. Examples of the material of the metal thin film include Au, Ti, Cu, Co, Pt, Al, and Cr. Examples of the material of the conductive oxide thin film include indium tin oxide (ITO), fluorine-doped tin oxide (FTO), and aluminum-doped zinc oxide (AZO). Examples of materials for conductive polymer thin films include poly(3,4-ethylenedioxythiophene), poly(3,4-ethylenedioxythiophene)-poly(4-styrene sulfonic acid), and polythiophene-based polymers, polybithiophene-based polymers, polyisothiophene-based polymers, polydodecylthiophene-based polymers, polyisonitethiophene-based polymers, poly-3-hexylthiophene-based polymers, polyacene-based polymers, polyparaphenylene-based polymers, polyaniline-based polymers, polydiacetylene-based polymers, polypyrrole-based polymers, and polyaniline-based polymers. When the flexible device 1 is used, if the source electrode 3 and the drain electrode 4 do not come into contact with living tissue, the materials of the source electrode 3 and the drain electrode 4 need not have biocompatibility.

The thickness of the source electrode 3 and the drain electrode 4 is typically from 10 nm to 1 μm.

The source electrode terminal 3a and the drain electrode terminal 4a are formed of a conductive thin film. The source electrode terminal 3a and the drain electrode terminal 4a are preferably formed of a metal thin film. Examples of the materials for the source electrode terminal 3a and the drain electrode terminal 4a include Au, Ti, Cu, Co, Pt, Al, and Cr.

The thickness of the source electrode terminal 3a and the drain electrode terminal 4a is typically from 10 nm to 500 nm.

The extended gate electrode 5 has a tip portion 5a (sensor portion) extended to a position away from the source electrode 3 and the drain electrode 4. The distance between the source electrode 3 and the drain electrode 4 and the tip portion 5a of the extended gate electrode 5 varies depending on the application, but is typically 2 cm or more, preferably from 2 cm to 5 cm.

The extended gate electrode 5 is formed of a carbon material thin film having biocompatibility and light transmissivity. The extended gate electrode 5 is more preferably formed of a carbon material thin film containing carbon atoms forming $sp^2$ hybrid orbitals. The extended gate electrode 5 is particularly preferably a graphene film. Examples of the graphene film include a single-layer graphene film and a multilayer graphene layer including 2 to 10 layers.

The extended gate electrode 5 preferably has an adhesion ratio of nerve cells of 50% or more as measured by the following method. The extended gate electrode 5 having an adhesion ratio of nerve cells of 50% or more has a high affinity for general cells and thus has high biocompatibility.

Method for Measuring Adhesion Ratio of Nerve Cells 1 mL of a nerve cell suspension is dropped onto the extended gate electrode and allowed to stand for 24 hours in a constant temperature bath adjusted to a temperature of 37° C. and a relative humidity of 100%. After standing, the nerve cell suspension on the glass substrate is removed and phosphate buffered saline is added. Next, cells on the glass substrate are stained with trypan blue, the numbers of live cells and dead cells of nerve cells are counted, and a proportion of the number of live cells to the total number of cells is calculated as an adhesion ratio of nerve cells.

The extended gate electrode 5 preferably has a light transmittance of 70% or more, and particularly preferably 90% or more, in a wavelength range of from 300 nm to 4 μm. By using the extended gate electrode 5 having such biocompatibility and light transmissivity, it is possible to simultaneously perform electrical measurement of living tissue and optical observation or light irradiation of living tissue.

The extended gate electrode 5 may have the surface of the tip portion 5a modified depending on the application. For example, when a specific antigen is to be captured by an antigen-antibody reaction using the extended gate electrode 5, the surface of the tip portion 5a of the extended gate electrode 5 may be modified by an antibody that binds to a specific antigen or an aptamer that selectively binds to an antigen to be detected. Further, for example, when used as a detector of an odor sensor, the surface of the tip portion 5a of the extended gate electrode 5 may be modified with an odor receptor.

The channel 6 is formed of an organic semiconductor thin film. That is, the flexible device 1 has an organic FET structure. The organic semiconductor thin film may be an n-type semiconductor or a p-type semiconductor. The organic semiconductor may be rubrene, C60 (fullerene), or P3HT (polyhexylthiophene).

Organic semiconductor thin films have a higher productivity than inorganic thin films such as silicon thin films, which are widely used as FET channels, and are rich in variety, soft, and highly flexible. Therefore, any type of the channel 6 (organic semiconductor thin film) can be easily formed on the insulating substrate 2.

The shape of the channel 6 is not particularly limited, but is typically a quadrangle. The length and width of the channel 6 vary depending on the sizes of the source electrode 3 and the drain electrode 4, but are typically from 50 μm to 500 μm.

The gate dielectric 7 is formed of an ionic liquid or an ionic gel. The ionic liquid is a liquid in which an anion and a cation are paired. As the ionic liquid, for example, N,N,N-trimethyl-N-propylammonium bis(trifluoromethylsulfonyl)imide ($DEME^+/TFSI^-$), N-methyl-N-propylpyrrolidinium bis(trifluoromethylsulfonyl)imide ($P13^+/TFSI^-$), 1-ethyl-3-methylimidazolium bis(trifluoromethylsulfonyl)imide ($EMIM^+/TFSI^-$), or 1-ethyl-3-methylimidazolium tetrafluoroborate ($EMIM^+/BF_4^-$) may be used; however, it is preferable to select the ionic liquid by paying attention to the side chain length of the cation forming the ionic liquid and the miscibility of the anion species with the organic solvent or water. For example, if miscibility with organic solvents is important, it is preferable that the side chain of the cation be long enough to be sufficiently dissolved in an organic solvent, and the anion contain (trifluoromethylsulfonyl)imide ($TFSI^-$) and $PF_6^-$. On the other hand, if miscibility with water is important, it is preferable that the side chain of the cation be short enough to be miscible with water, and the anion contain $Cl^-$ and $CF_3COO^-$. Typically, there is a trade-off between the drive voltage of an organic FET and charge mobility, but even $P13^+/TFSI^-$, which is said to exhibit high charge mobility, exhibits a low drive voltage of 0.2 V or less, so most organic FETs function as biosensors with sufficient sensitivity when using an ionic liquid or ionic gel as a gate dielectric.

The ionic gel is a gel-like substance containing an ionic liquid and is generally obtained by mixing a copolymer with an ionic liquid, dissolving the copolymer in a solvent, and then volatilizing the solvent. The solvent used is not particularly specified, but typically an organic solvent such as acetone, acetonitrile, ethyl acetate, hexane, or toluene is used. The copolymer used is not particularly specified, and typical examples thereof include a methyl methacrylate/styrene copolymer (PS-PMMA-PS) and a vinylidene fluoride hexafluoropropylene copolymer (PVDF-HFP). For example, a mixture of 50 μL of ionic liquid $EMIM^+/TFSI^-$ and 25 mg of PVDF-HFP is dissolved in 1 mL of acetonitrile and spin-coated or dropped onto a wafer or glass substrate. Then, the substrate is heated on a hot plate at a temperature of about 70° C. for about 10 minutes to volatilize the organic solvent (acetonitrile) to obtain an ionic gel on the surface of the substrate. Finally, the ionic gel is peeled off from the substrate. If necessary, the ionic gel is molded before and after peeling. It is also possible to control the film quality of the gel by changing the proportion of the ionic liquid and the copolymer. It is also possible to obtain an ionic gel by using cellulose instead of a copolymer.

The gate dielectric 7 formed of an ionic liquid and an ionic gel containing an ionic liquid has a thickness as thin as a cation molecule size (about 1 nm) constituting the ionic liquid. Therefore, by using the gate dielectric 7, it is possible to obtain the flexible device 1 having an organic FET structure that detects weak biological signals and chemical bonds with high sensitivity.

The protective layer 8 is a layer for protecting the ionic liquid constituting the gate dielectric 7 so as not to be washed away. The material of the protective layer 8 is not particularly limited, but a silicone resin is preferable. For example, a polydimethylsiloxane (PDMS) resin or a polyparaxylene resin may be used. From the viewpoint of flexibility and processability, a polydimethylsiloxane resin is preferable.

In the flexible device 1 of the present embodiment having the above configuration, the insulating substrate 2 is formed of a flexible thin film having light transmissivity, the extended gate electrode 5 is formed of a carbon material thin film having biocompatibility and light transmissivity, the channel 6 is an organic semiconductor thin film, and the gate dielectric 7 is formed of an ionic liquid or an ionic gel, so that the flexible device 1 can simultaneously perform electrical measurement of living tissue and optical observation or light irradiation of living tissue. In addition, electrical measurement can be performed with high sensitivity.

The flexible device 1 of the above embodiment is merely an example of the present invention, and the present invention is not limited to the above embodiment. For example, in the flexible device 1 of the present embodiment, the source electrode 3 includes a source electrode terminal 3a, and the drain electrode 4 includes a drain electrode terminal 4a, but the present invention is not limited thereto. The source electrode 3 and the drain electrode 4 may be directly connected to a device for measuring an electrical signal of a living body. In the flexible device 1 of the present embodiment, the protective layer 8 for covering the gate dielectric 7 is provided, but the protective layer 8 need not be provided if the ionic liquid or ionic gel constituting the gate dielectric 7 has a high viscosity and consequently does not flow out easily. Further, in the flexible device 1 of the present embodiment, the tip portion 5a of the extended gate electrode 5 has a wide width, but the width of the tip portion 5a is not particularly limited, and if there is no problem in measuring the electric signal, the width of the tip portion 5a does not need to be widened, and the width of the tip portion 5a may be narrower than other portions.

Next, a method for producing the flexible device 1 according to the embodiment of the present invention will be described. The method for producing the flexible device 1 according to the present embodiment includes preparing a laminate to be a raw material; electrode forming of forming a source electrode, a drain electrode, and an extended gate electrode using the laminate; channel forming of forming a channel at an interval between the source electrode and the drain electrode; and gate dielectric forming of applying a gate dielectric to cover all of the channel and a portion of the extended gate electrode. Hereinafter, the method for producing the flexible device 1 according to the present embodiment will be described with reference to FIGS. 3 to 9. In FIGS. 3 to 9, (a) are plan views, and (b) are sectional views taken along the line (b)-(b) in each (a).

Figure 3:
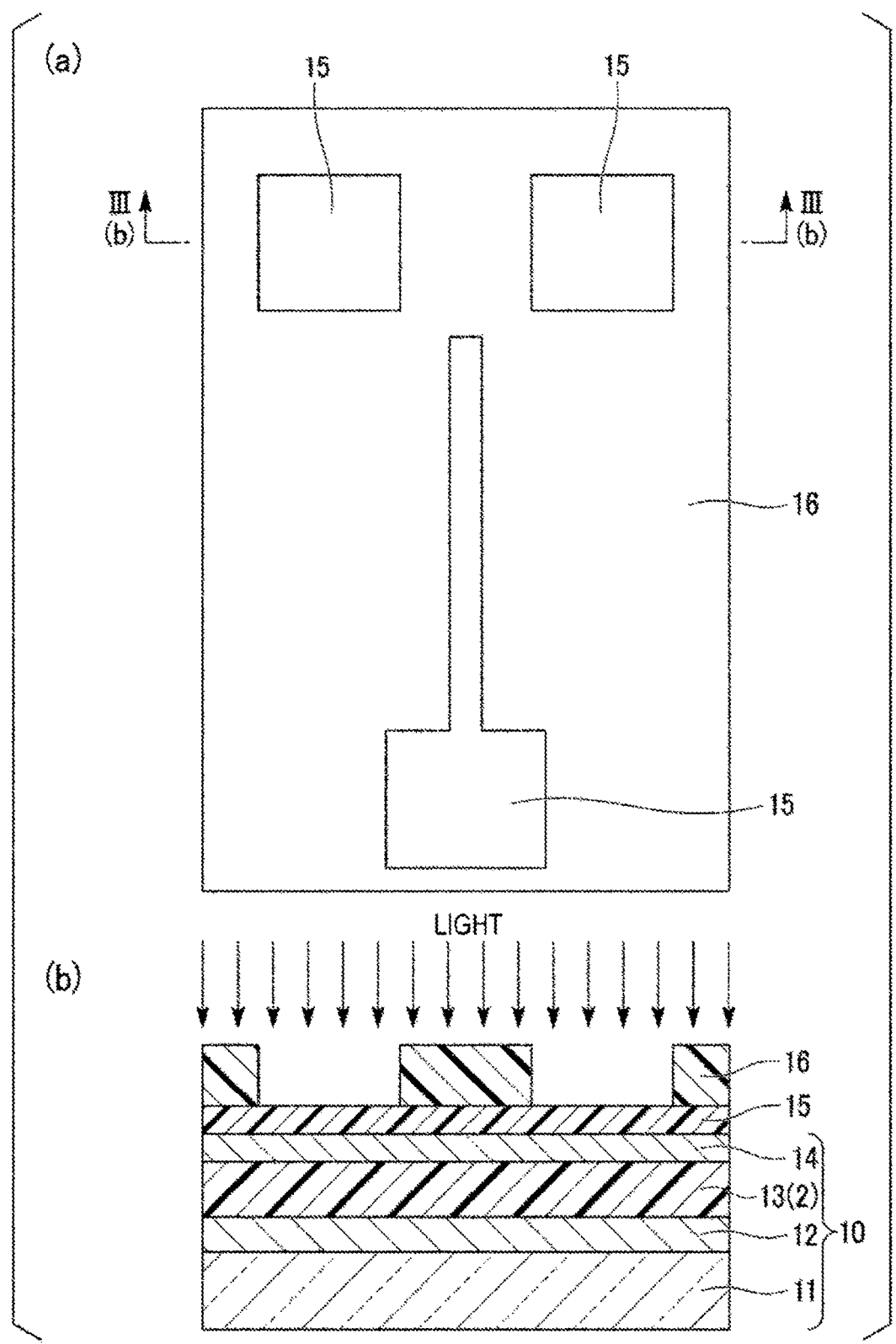

In the preparing, as illustrated in FIG. 3, a laminate 10 in which a sacrificial layer 12, the flexible thin film 13 having light transmissivity, and a carbon material thin film 14 are laminated in this order is prepared on a solid substrate 11.

The solid substrate 11 is a substrate used when producing a flexible device. The solid substrate 11 is a substrate having a flat surface, and a substrate used in a typical semiconductor process may be used. The material of the solid substrate 11 is not particularly limited, and glass, silicon, or plastic may be used. The thickness of the solid substrate 11 is preferably from 0.3 mm to 1 mm.

The sacrificial layer 12 is a layer that can be removed by a chemical or physical method and is a layer for facilitating peeling of the flexible device from the solid substrate 11 by removing the layer after the flexible device 1 has been produced. The material of the sacrificial layer 12 may be of any type as long as it can be removed without damaging the produced flexible device. The material of the sacrificial layer 12 may be a metal or an organic substance. Examples of the metal include aluminum, iron, and copper. Aluminum and iron can be removed by, for example, immersion in an aqueous sodium hydroxide solution (concentration 1 M) or Microposit (trade name) 351 Developer for about 1 to 5 minutes. Copper can be quickly removed by immersion in, for example, a solution in which equal amounts of aqueous ammonia (3M) and aqueous hydrogen peroxide (from 3 to 30%) are mixed. Copper can also be removed by using an aqueous solution of 1 to 5 g of sodium chloride and 4 to 10 mL of hydrogen peroxide solution (from 3 to 30%) added to an aqueous solution of sodium glutamate (from 1 to 5 g/20 mL) or by using an aqueous solution of iron (III) chloride. The method for forming the sacrificial layer 12 formed of a metal is not particularly limited, and a sputtering method, an EB vapor deposition method, or the like can be used.

An example of an organic substance used as the material of the sacrificial layer 12 is gelled sodium alginate. The sacrificial layer 12 using gelled sodium alginate can be formed, for example, by filtering an aqueous sodium alginate solution (1% wt) with a hydrophilic filter (200 nm pore diameter), applying it to the surface of the solid substrate 11 using a spin coating method (for example, at 3000 rpm for 30 seconds), and then immersing the obtained coating film in an aqueous calcium chloride solution (0.1 M) for 10 seconds in order to gel. The sacrificial layer 12 using this gelled sodium alginate can be removed by using EDTA (5 mM). Since the sacrificial layer 12 using the gelled sodium alginate can be removed by using EDTA which is harmless to biomolecules, it is preferable when producing a flexible device in which an extended gate electrode is modified by a biomolecule such as a protein.

The film thickness of the sacrificial layer 12 is typically from 10 nm to 200 nm.

The flexible thin film 13 is a film that constitutes the insulating substrate 2 of the flexible device 1. When the insulating substrate 2 is a polyparaxylene resin film, a thin-film deposition method can be used as a method for forming the insulating substrate 2.

The carbon material thin film 14 is a film constituting the source electrode 3, the drain electrode 4, and the extended gate electrode 5 of the flexible device 1. When the carbon material thin film 14 is a graphene film, a transfer method can be used as a method for forming the carbon material thin film 14. The transfer method is a method in which a graphene film is formed on a surface of a separately prepared transfer substrate, and the graphene film formed on the surface of the transfer substrate is transferred to a surface of the flexible thin film 13.

In the electrode forming, as illustrated in FIG. 3, a negative resist layer 15 is laminated over the entire surface of the carbon material thin film 14 of the laminate 10, and then a mask 16 having a predetermined pattern is formed. The mask 16 having a predetermined pattern can be formed, for example, by processing a photocurable resin with a 3D printer. In the case of a mask obtained by a 3D printer, since the pattern portion becomes an opening portion, it is desirable to use a negative resist in which the resist of the exposed and developed portion remains. After forming the mask 16, the surface of the negative resist layer 15 is exposed and developed to remove the portion of the negative resist layer 15 not covered with the mask 16, and then the mask 16 is removed. As a result, as illustrated in FIG. 4, negative resist layers 15a, 15b, and 15c having a predetermined pattern are formed.

Figure 4:
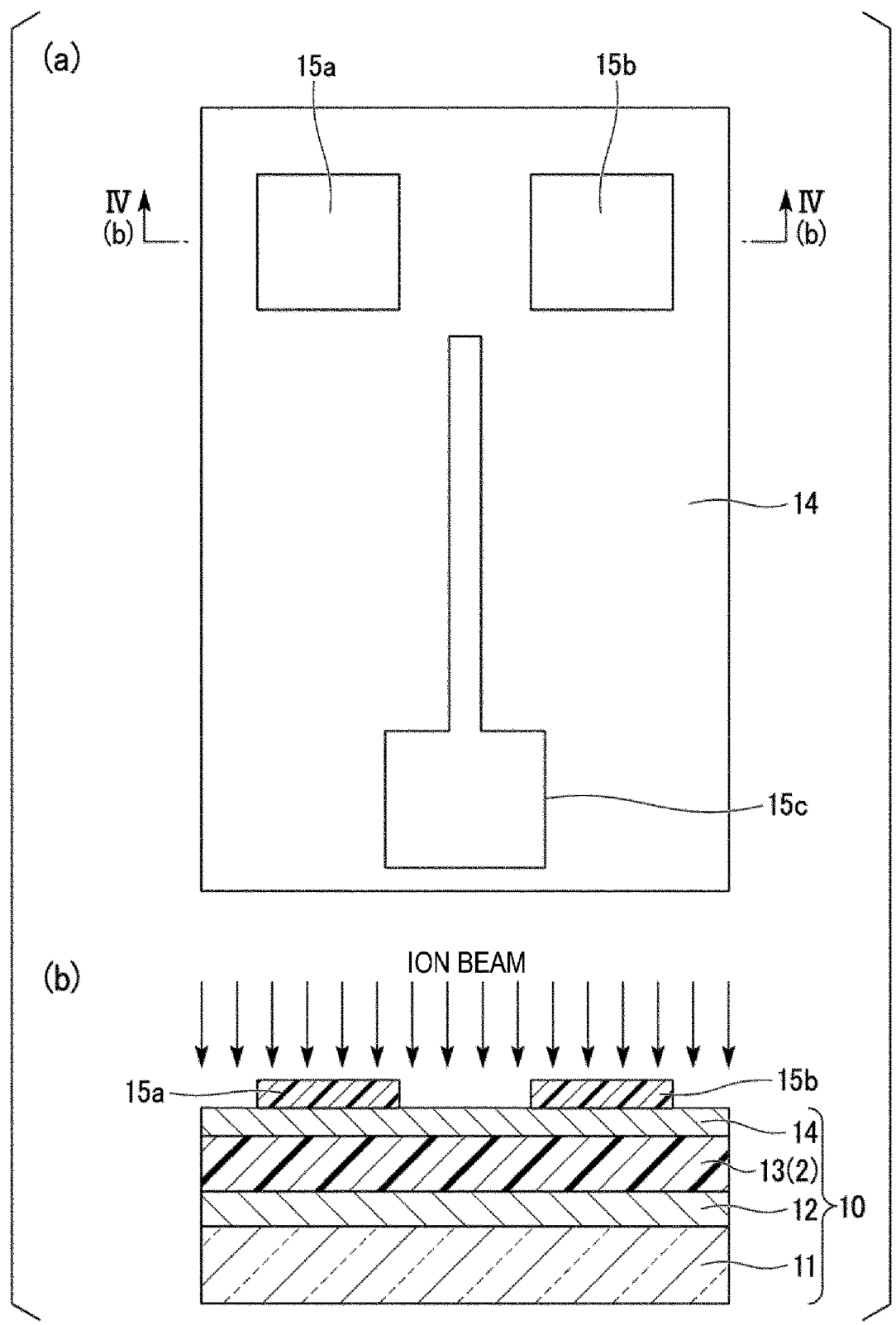
Figure 5:
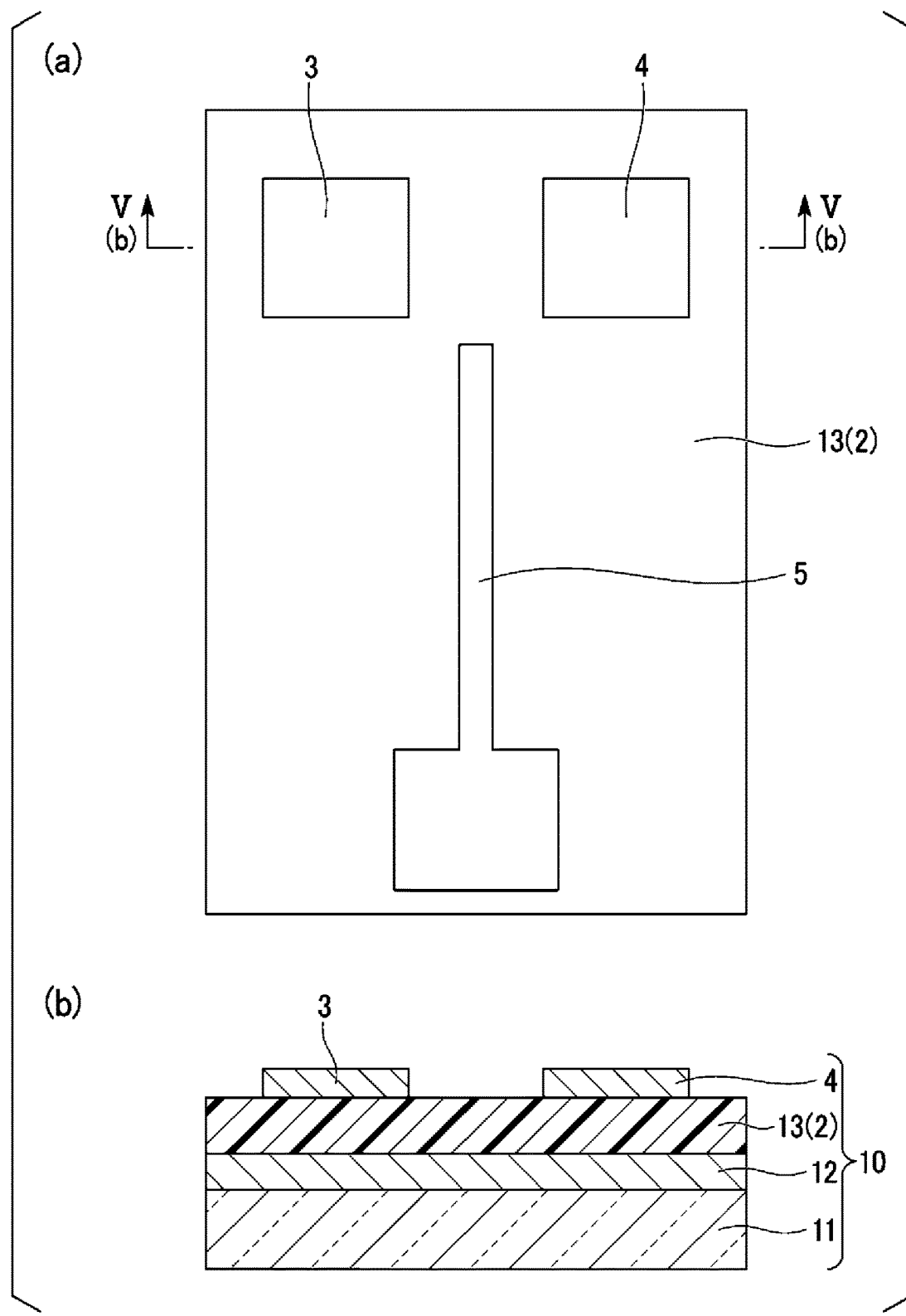

Next, as illustrated in FIG. 4, the surface of the laminate 10 is irradiated with an ion beam. As a result, the portion of the carbon material thin film 14 that is not covered with the negative resist layers 15a, 15b, and 15c is removed. Then, the negative resist layers 15a, 15b, and 15c are removed with an organic solvent such as acetone. As a result, as illustrated in FIG. 5, the source electrode 3, the drain electrode 4, and the extended gate electrode 5 formed of the carbon material thin film 14 are formed.

Figure 6:
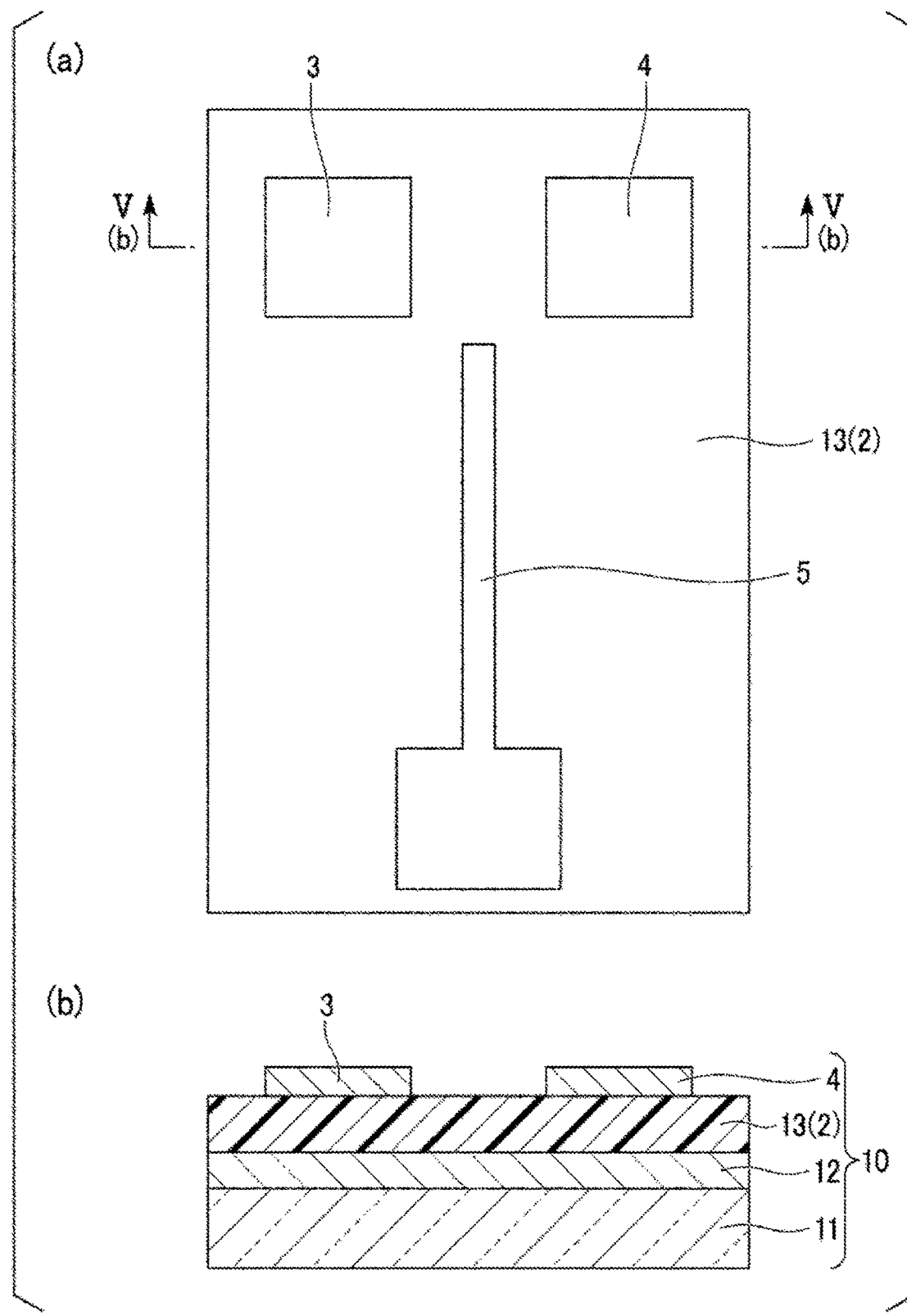

In the channel forming, first, as illustrated in FIG. 6, the surface region other than the interval between the source electrode 3 and the drain electrode 4 of the laminate 10 is covered with a mask 17. Next, an organic semiconductor thin film 18 is formed on the portion not covered with the mask 17. The organic semiconductor thin film 18 is a film that constitutes the channel 6 of the flexible device 1. The method for forming the organic semiconductor thin film 18 is not particularly limited, and the organic semiconductor thin film 18 can be formed by any method such as a casting method or a spin coating method.

Figure 7:
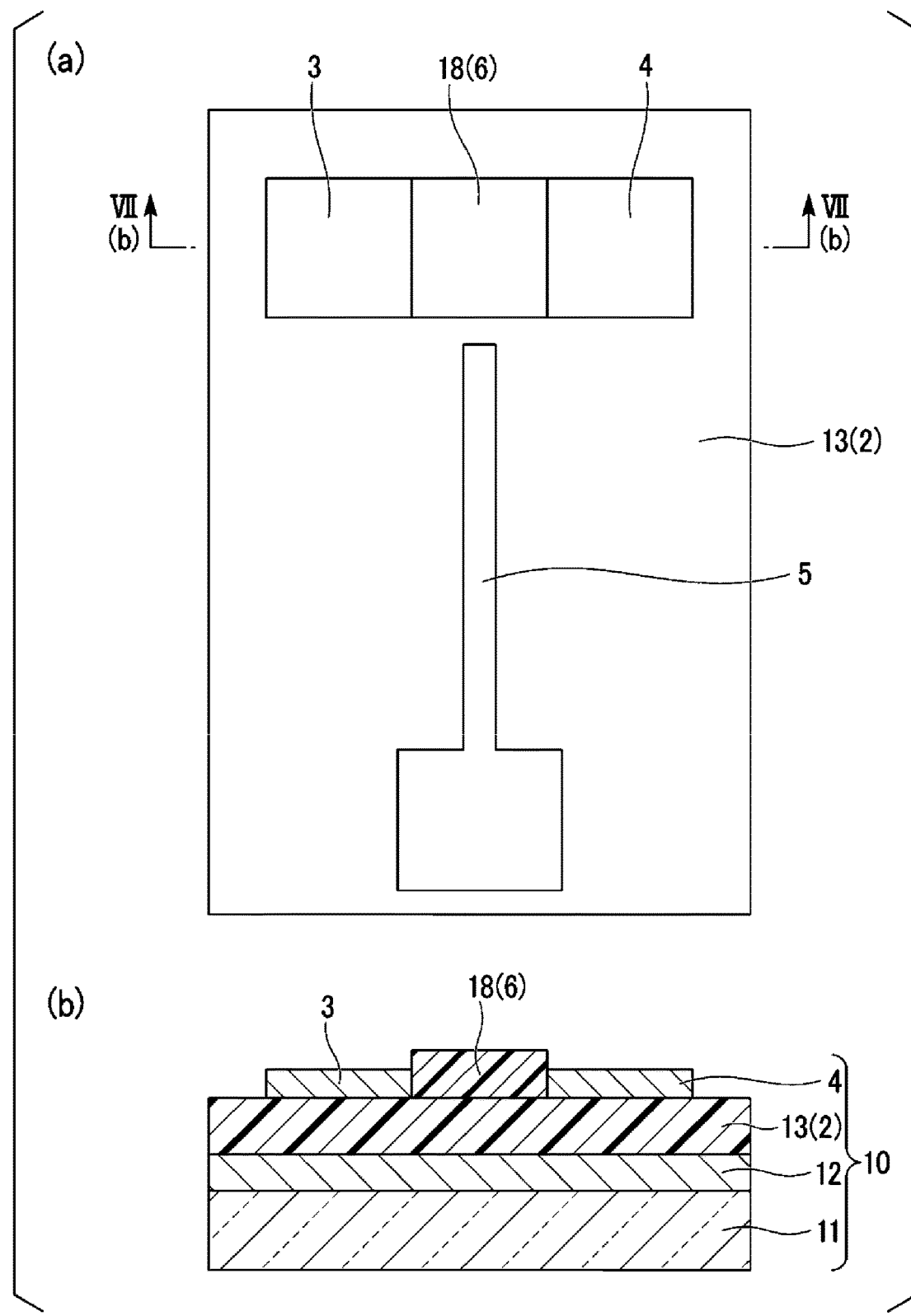

Next, as illustrated in FIG. 7, the mask 17 is removed, and it is confirmed that the organic semiconductor thin film 18 is formed in the interval between the source electrode 3 and the drain electrode 4.

Figure 8:
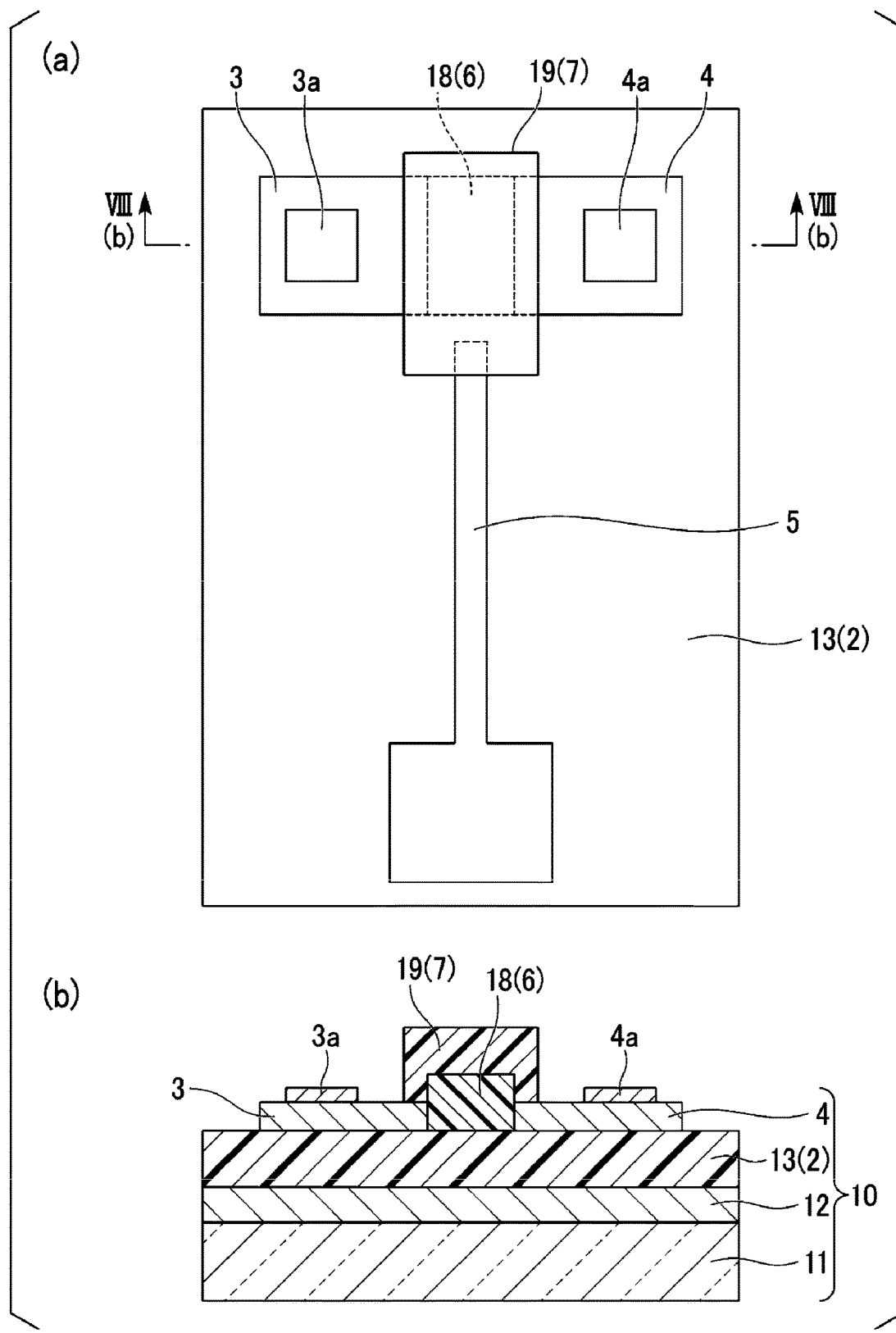

In the gate dielectric forming, as illustrated in FIG. 8, an ionic liquid 19 is applied so as to cover the entire surface of the organic semiconductor thin film 18 (channel 6) and a part of the extended gate electrode 5. An ionic gel may be used instead of the ionic liquid 19. The ionic liquid 19 constitutes the gate dielectric 7 of the flexible device 1. The application method of the ionic liquid 19 is not particularly limited, and a point application method can be used.

As illustrated in FIG. 8, the source electrode terminal 3a is formed on the source electrode 3, and the drain electrode terminal 4a is formed on the drain electrode 4. The source electrode terminal 3a and the drain electrode terminal 4a may be formed by any method such as a vapor deposition method or a sputtering method. The source electrode terminal 3a and the drain electrode terminal 4a are preferably formed before the application of the ionic liquid 19.

Figure 9:
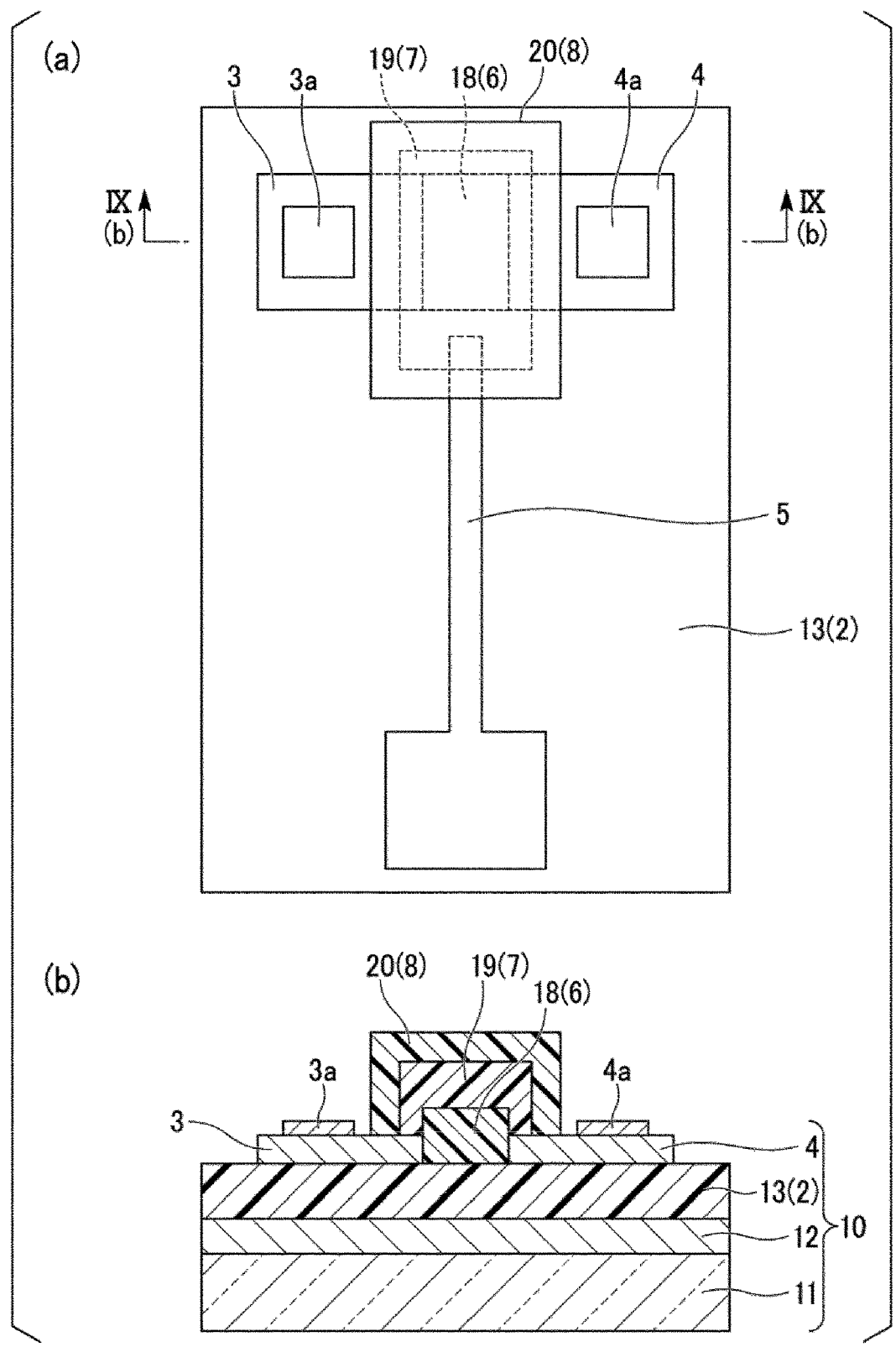

Next, as illustrated in FIG. 9, a protective material film 20 is formed so as to cover the ionic liquid 19 (gate dielectric 7). The protective material film 20 constitutes the protective layer 8 of the flexible device 1. The method for forming the protective material film 20 is not particularly limited, and when the protective material film 20 is a polydimethylsiloxane (PDMS) resin film, laser processing or molding by a mold may be applied.

Finally, the sacrificial layer 12 is removed, and the solid substrate 11 and the flexible thin film 13 (insulating substrate 2) are peeled off.

According to the method for producing the flexible device 1 according to the present embodiment having the above configuration, the flexible device 1 can be profitably produced.

The method for producing the flexible device 1 of the above embodiment is merely an example of the present invention, and the present invention is not limited to the above embodiment. For example, in the method for producing the flexible device 1 of the present embodiment, the mask 16 is formed by processing with a 3D printer, but the mask 16 may be a photomask. In the case of a photomask, both positive and negative resists may be used depending on the mask specifications.

Figure 10:
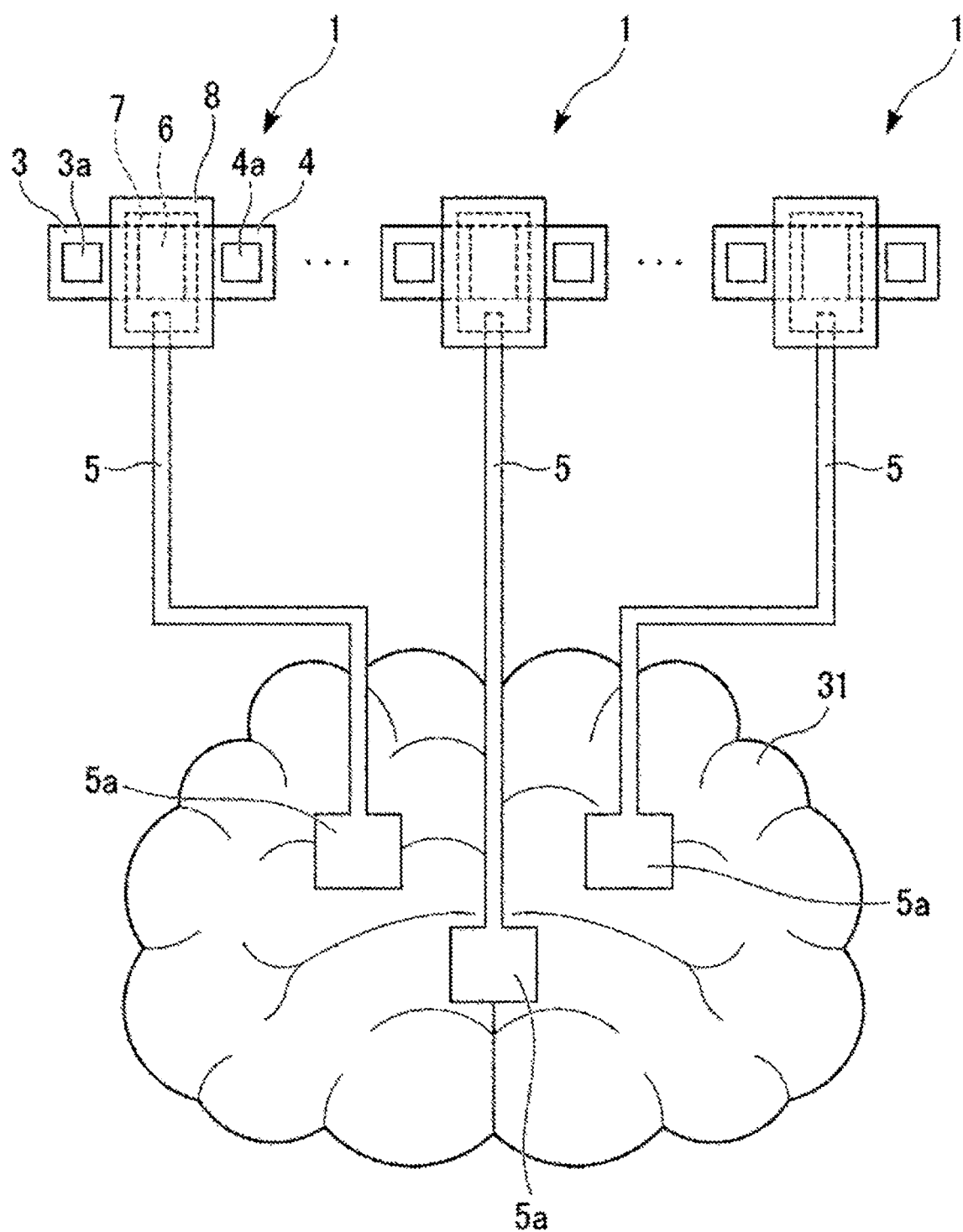
FIG. 10 conceptually illustrates an example of a usage state of a flexible device according to an embodiment of the present invention.

Next, a method for using the flexible device 1 according to the present embodiment will be described. FIG. 10 conceptually illustrates an example of a usage state of the flexible device according to the embodiment of the present invention.

In the usage state illustrated in FIG. 10, three flexible devices 1 are used to electrically measure brain tissue 31 and optically observe the brain tissue 31. The tip portions 5a of the extended gate electrodes 5 of the three flexible devices 1 are each connected to the brain tissue 31. The drain voltage of each of the flexible devices 1 is constant, and when the tip portions 5a of the extended gate electrode 5 sense a change in voltage from the brain tissue 31 as a change in gate voltage, the drain current changes following the change in gate voltage. By measuring this drain current, the change in the electrical signal of the brain tissue 31 is measured. As illustrated in FIG. 10, the source electrode 3, the drain electrode 4, and the channel 6 are preferably arranged at positions that do not come into contact with the in vivo tissue.

Since the extended gate electrode 5 of the flexible device 1 has light transmissivity, the flexible device 1 can measure an electrical signal of the brain tissue 31, optically observe the brain tissue 31, and measure a change in the electrical signal when light is applied. Therefore, by using the flexible device 1 of the present embodiment, various information can be obtained as compared with the related-art flexible device.

Figure 11:
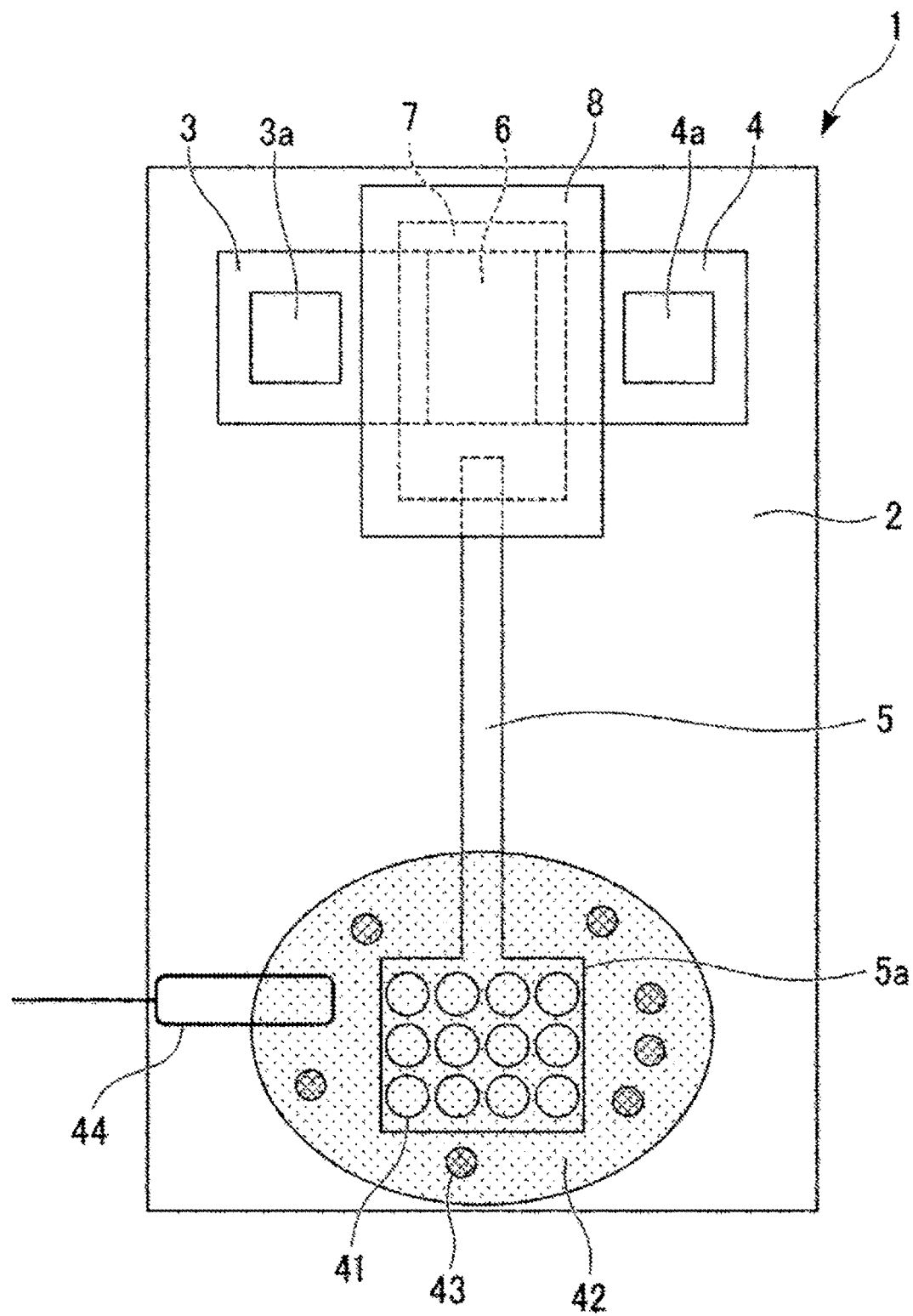
FIG. 11 conceptually illustrates another example of a usage state of a flexible device according to an embodiment of the present invention.

FIG. 11 conceptually illustrates another example of the usage state of the flexible device according to the embodiment of the present invention.

In the usage state illustrated in FIG. 11, using one flexible device 1, an antigen-antibody reaction between an antibody 41 immobilized on the tip portion 5a of the extended gate electrode 5 and an antigen 43 in a sample 42 is analyzed by electrical measurement and optical observation. A fluorescent substance (label) is bound to the antigen 43 in advance. The antibody 41 having an affinity for the antigen 43 is immobilized on the tip portion 5a of the extended gate electrode 5 of the flexible device 1. A constant voltage is applied to the extended gate electrode 5, and the sample 42 is dropped onto the tip portion 5a of the extended gate electrode 5. If necessary, a reference electrode 44 (typically a silver/silver chloride electrode) is placed in the sample 42. When an antibody-antigen reaction occurs and the antigen 43 binds to the antibody 41, the drain current changes due to a change in an interfacial potential between the extended gate electrode 5 and the sample 42. By measuring the drain current and observing the fluorescence of the phosphor bound to the antigen 43, the antigen-antibody reaction can be analyzed from two types of information, an electric signal and light. If an aptamer that selectively binds to the antigen of interest is available, it may be used instead of the antibody.

The method of using the flexible device 1 of the present embodiment has been described above; however, the method of using the flexible device 1 is not limited to the above embodiment. The flexible device 1 can be used, for example, as a biodevice for measuring an electrical signal of a living body in a wearable system such as a skin-attached device of a biosensor. The flexible device 1 can also be used as a detector that captures and detects an odor component for an odor sensor.

REFERENCE SIGNS LIST

1 Flexible device
2 Insulating substrate
3 Source electrode
3a Source electrode terminal
4 Drain electrode
4a Drain electrode terminal
5 Extended gate electrode 5a Tip portion
6 Channel
7 Gate dielectric
8 Protective layer
10 Laminate
11 Solid substrate
12 Sacrificial layer
13 Flexible thin film
14 Carbon material thin film
15a, 15b, 15c Negative resist layer
16, 17 Mask
18 Organic semiconductor thin film
19 Ionic liquid
20 Protective material film
31 Brain tissue
41 Antibody
42 Sample
43 Antigen
44 Reference electrode

The invention claimed is:

1. A flexible device comprising:
an insulating substrate;
a source electrode, a drain electrode, and an extended gate electrode formed on a surface of the insulating substrate at intervals, the extended gate electrode including a first portion and a tip portion extending away from the source electrode and the drain electrode, a dimension between the source electrode and the drain electrode to the tip portion being greater than 2 centimeters;
a channel arranged at an interval between the source electrode and the drain electrode; and
a gate dielectric formed so as to cover all of the channel and the first portion of the extended gate electrode,
wherein the insulating substrate is a flexible thin film having light transmissivity,
the extended gate electrode is a carbon material thin film having biocompatibility and light transmissivity,
the channel is an organic semiconductor thin film,
the gate dielectric is an ionic liquid or an ionic gel,
the tip portion of the extended gate electrode is configured to contact a tissue,
the flexible device is configured to measure the electrical signal of the tissue by measuring a change in drain current, and a drain voltage of the drain electrode is constant, a gate voltage of the extended gate electrode changes in response to a change in electrical signal of the tissue, and the drain current changes in response to the change in gate voltage.

2. The flexible device according to claim 1, wherein the insulating substrate has a light transmittance of 70% or more in a wavelength range of from 300 nm to 4 μm.

3. The flexible device according to claim 1, wherein the extended gate electrode is a carbon material thin film including carbon atoms with $sp^2$ hybrid orbitals.

4. The flexible device according to claim 3, wherein the extended gate electrode is a graphene film.

5. The flexible device according to claim 1, wherein the extended gate electrode has a light transmittance of 70% or more in a wavelength range of from 300 nm to 4 μm.

6. The flexible device according to claim 1, wherein the extended gate electrode has an adhesion ratio of nerve cells of 50% or more.

7. The flexible device according to claim 1, wherein the flexible device is adapted to be worn by a user.

8. The flexible device of claim 1, wherein the electrical signal of the tissue changes in response to light.

9. A method for producing a flexible device, comprising:
preparing a laminate having a flexible thin film having light transmissivity and a carbon material thin film having biocompatibility and light transmissivity laminated on a surface of the flexible thin film;
forming a source electrode, a drain electrode, and an extended gate electrode by removing a part of the carbon material thin film of the laminate;
forming an organic semiconductor thin film at an interval between the source electrode and the drain electrode; and
applying an ionic liquid or an ionic gel so as to cover all of the organic semiconductor thin film and a part of the extended gate electrode,
wherein the flexible device comprises:
the flexible thin film configured to be an insulating substrate;
the source electrode, the drain electrode, and the extended gate electrode, the extended gate electrode including a first portion and a tip portion extending away from the source electrode and the drain electrode, a dimension between the source electrode and the drain electrode to the tip portion being greater than 2 centimeters;
the organic semiconductor thin film; and
the ionic liquid or the ionic gel covering all of the organic semiconductor thin film and the first portion of the extended gate electrode,
wherein the tip portion of the extended gate electrode is configured to contact a tissue,
wherein the flexible device is configured to measure an electrical signal of the tissue by measuring a change in drain current, and a drain voltage of the drain electrode is constant, a gate voltage of the extended gate electrode changes in response to a change in electrical signal of the tissue, and the drain current changes in response to the change in gate voltage.

10. The flexible device according to claim 1, wherein the insulating substrate is a polyparaxylene resin.

11. The flexible device according to claim 1, wherein the insulating substrate has a thickness in the range of 1 micrometer to 3 micrometers.

12. The flexible device according to claim 1, wherein each of the source electrode and the drain electrode include a film material selected from the group consisting of: a metal, a metal oxide, a conductive polymer, carbon and combinations thereof.

13. The flexible device according to claim 1, wherein each of the source electrode and the drain electrode have a thickness in the range of 10 nanometers to 1 micrometer.

14. The flexible device according to claim 1, wherein the tissue is brain tissue.

15. A flexible device comprising:
an insulating substrate;
a source electrode, a drain electrode, and an extended gate electrode formed on a surface of the insulating substrate at intervals, the extended gate electrode including a first portion and a tip portion extending away from the source electrode and the drain electrode;
a channel arranged at an interval between the source electrode and the drain electrode; and
a gate dielectric formed so as to cover all of the channel and the first portion of the extended gate electrode,
wherein:
the insulating substrate is a flexible thin film having light transmissivity, the extended gate electrode is a carbon material thin film having biocompatibility and light transmissivity, the channel is an organic semiconductor thin film,
the gate dielectric is an ionic liquid or an ionic gel,
the tip portion of the extended gate electrode is configured to contact brain tissue,
the flexible device measures an electrical signal of the brain tissue by measuring a change in drain current, and
a drain voltage of the drain electrode is constant, a gate voltage of the extended gate electrode changes in response to a change in electrical signal of the brain tissue, and the drain current changes in response to the change in gate voltage.

16. The flexible device of claim 15, wherein the electrical signal of the brain tissue changes in response to light.

* * * * *